United States Patent [19]
Nishimura et al.

[11] Patent Number: 5,698,790
[45] Date of Patent: Dec. 16, 1997

[54] METHOD FOR MEASURING ADHESION STRENGTH OF RESIN MATERIAL

[75] Inventors: Asao Nishimura, Ushiku; Naotaka Tanaka, Ibaraki-ken; Isao Hirose, Toyohashi, all of Japan

[73] Assignee: Hitachi, Ltd., Tokyo, Japan

[21] Appl. No.: 646,141

[22] Filed: May 7, 1996

Related U.S. Application Data

[62] Division of Ser. No. 287,593, Aug. 8, 1994, Pat. No. 5,537,884, which is a division of Ser. No. 62,543, May 18, 1993, Pat. No. 5,359,899.

[30] Foreign Application Priority Data

May 18, 1992 [JP] Japan ................................. 4-124503

[51] Int. Cl.⁶ .................................................. G01N 3/24
[52] U.S. Cl. .................................................. 73/842
[58] Field of Search .................. 73/150 A, 826, 73/827, 841, 842, 845, 849, 851, 852

*Primary Examiner*—Robert Raevis
*Attorney, Agent, or Firm*—Antonelli, Terry, Stout & Kraus, LLP.

[57] ABSTRACT

A method for measuring an adhesion strength of a resin material which is capable of accurately and readily measuring a universal adhesion strength independent of dimensions and shapes of specimen. A delamination portion is partially formed between a resin and an adherend material. Loads in two different directions are applied to an adhering interface such that opposed shear stresses are generated. As a result, a true adhering strength can be obtained from an apparent delamination propagating strength in each case.

8 Claims, 8 Drawing Sheets

FIG. 9

| | TEST RECORDS | | | |
|---|---|---|---|---|
| NAME | HMRL - 011 | SERIAL NUMBER | | 91 - 06845 |
| DATA OF ISSUE | | OCTOBER 18,1991 | | |

| TEST ITEMS | CONDITIONS | UNIT | TEST METHOD | TEST RESULT |
|---|---|---|---|---|
| SPIRAL FLOW | 170°C | cm | — | 85 |
| GEL TIME | 170°C | s | CARAST METER | 25 |
| SPECIFIC GRAVITY | — | — | JIS K6911 | 1.80 |
| COEFFICIENT OF LINEAR EXPANSION $\alpha_1$ | — | $\times 10^{-6}$/°C | TMA | 15 |
| COEFFICIENT OF LINEAR EXPANSION $\alpha_2$ | — | $\times 10^{-6}$/°C | TMA | 74 |
| GLASS TRANSITION TEMPERATURE | — | °C | TMA | 171 |
| HEAT CONDUCTIVITY | — | W/(m·k) | — | 0.67 |
| BENDING ELASTIC MODULUS | 20°C | GPa | JIS K6911 | 15.3 |
| BENDING STRENGTH | 20°C | MPa | JIS K6911 | 131 |
| ADHESION STRENGTH $K_1$ | 20°C 42 ALLOY | MPa$\sqrt{m}$ | SHEAR STRESS INVERSION METHOD | 1.43 |
| VOLUME RESISTIVITY | 20°C | $\Omega$·cm | JIS K6911 | $9.5 \times 10^{15}$ |
| VOLUME RESISTIVITY | 100°C | $\Omega$·cm | JIS K6911 | $7.0 \times 10^{14}$ |
| DIELECTRIC CONSTANT | 1MHz | — | JIS K6911 | 4.2 |
| ELECTRIC CONDUCTIVITY OF EXTRACTED WATER | — | $\mu$S/cm | — | 64 |
| EXTRACTED WATER PH | — | — | — | 4.0 |
| U CONTENT | — | ppb | — | 0.2 |

METHOD FOR MEASURING ADHESION STRENGTH OF RESIN MATERIAL

This application is a divisional application of Ser. No. 08/287,593, filed Aug. 8, 1994, now U.S. Pat. No. 5,537, 884, which is a Divisional application of Ser. No. 08/062, 543, filed May 18, 1993 now U.S. Pat. No. 5,359,899.

BACKGROUND OF THE INVENTION

1. Field of the Invention

The present invention relates to a display method, a container, a carrying document, an adhesion strength measuring method, and a composite manufacturing method for resin material (resin composition), and more particularly to a display method, a container, a carrying document, an adhesion strength measuring method and a composite manufacturing method for resin material (resin composition) which is capable of providing a universal adhesion strength regardless of dimensions and configuration of adhering specimens, and further to a resin material (resin composition), the adhering reliability of which can be easily evaluated.

2. Description of the Related Art

In resin-molded electronic and electric parts containing inserting components such as resin encapsulated semiconductor devices and resin insulating transformers, the interfaces between the resin and the inserting components are subjected to high residual stress due to cure shrinkage of the resin and thermal expansion mismatch between the resin and the inserting components.

Further, the internal exothermic action and the harsh heating/cooling operations increase the thermal stress which sometimes causes delamination during operations of the components and reliability tests.

Such a delamination at adhering interfaces not only results in corrosion of electric wiring materials and electric insulating degradation, but also causes a variety of other damages, such as cracking of the resin and wire breaking due to the stress concentration by the delamination.

The evaluation of resin material adhesion strength is therefore a critical issue in assuring the reliability of such resin-molded components.

Conventional methods for measuring the adhesion strength of resin material apply tensile or shear loads to an adhering specimen, and then divide the obtained fracture (delamination) loads by the adhesion area or length as described in IEEE Transactions on Comp., Hybrids, Manuf. Technol., Vol. 14, No. 4 (1991) pp. 809–817 and in Adhesion Technology, Vol. 9, No. 1 (1990) pp. 60–63 and 64–75.

Another method is disclosed in the Proceedings of the 67th Spring Annual Meeting of the Japan Society of Mechanical Engineers Ser. A (1990), pp. 75–77. In this method, a load is applied to an adhering specimen having partly formed delaminating portions, and a stress distribution near the delamination tip, i.e. near the boundary between the delaminating portion and the adhering portion, at the onset of delamination propagation is described by fracture mechanics parameter.

Further, other method is disclosed in the Transactions of the Japan Society of Mechanical Engineers, Ser. A, Vol. 54, No. 499 (1988) pp. 597–603. In this method, a temperature at which delamination takes place due to a residual stress is measured during cooling process after molding an adhering specimen, and a residual stress distribution at the delamination onset portion at that time is analyzed.

Among aforementioned conventional arts, in the tensile/shear loads applying method there is present the residual stress already when the adhering specimen is made. Therefore, the measurable adhesion strength would be nothing more than an apparent adhesion strength, which is a superimposition of the residual stress on the true adhesion strength.

Particularly in the case of semiconductor transfer molding resin for semiconductor encapsulation, the adhesion strength is relatively low due to a mold release agent contained in the resin material for easily parting from molding die. As a result, the reduction rate of the adhesion strength caused by the residual stress becomes large, such that the residual stress sometimes causes by itself the delamination at the interface.

Even if the adhesion strength measured by such a method is compared to an interface stress obtained by analysis or experiment, the adhering reliability of the resin molded components cannot be evaluated.

Further, the stress at the adhering interface is not uniform, but has singularity so as to become infinite at the end portions.

All the distributions of the residual stress and the stress caused by the load application during the adhesion test depend on the dimensions, shapes and materials of the specimens. Accordingly, in such conventional methods, as dividing the load by the adhering area on the assumption that the stress is uniformly distributed, dividing the load by the adhering length on the assumption that the load acts only on a line along the delamination front, the resulting adhesion strength depends on the dimensions, shapes etc. of the specimens, such that no universal measured value can be obtained.

If there is no residual stress, it is possible to obtain a universal adhesion strength by a method of describing a stress distribution near a singular point such as delamination tip by use of fracture mechanics parameters. On the other hand, however, in the case of the residual stress being present, the residual stress distribution must be obtained by analysis, as in the aforementioned last reference, the Transactions of the Japan Society of Mechanical Engineers, Ser. A, Vol. 54, No. 499 (1988) pp. 597–603. The analysis of the residual stress would be sometimes quite complicated or difficult to be performed with high accuracy due to conspicuous temperature dependency of the material properties or significant viscoelastic behavior at high temperatures depending on the materials of the resin composition.

Further, as in the case of the last reference, if the delamination is caused only by the residual stress, there would be a disadvantage that the adhesion strength may not be freely measured at any desired temperatures.

Thus, in the conventional methods, any universal adhesion strength as material property values could not be actually obtained. As a result, it is not possible to quantitatively predict the adhesion reliability of the interface of resin-molded products, such that the adhering state and adhesion strength etc. of the interface should be actually tested and measured by actually making the resin-molded products.

SUMMARY OF THE INVENTION

It is therefore an object of the present invention to provide a method for measuring adhesion strength of resin material which is capable of separating a true adhesion strength from a residual stress and of accurately and readily measuring a universal strength independent of dimensions and shapes of specimens, and to provide a display method, a container and a carrying document of the resin material, using the measured result and a manufacturing method of a composite body using the measured result.

It is another object of this invention to provide a resin material the adhesion reliability of which at its product interface can be readily predicted and evaluated from given material property values.

The first object can be attained by: making an adhering specimen having a partial delaminating portion between a resin material and an adherend requiring the adhesion strength and having a configuration as residual stress on the adhering interface near the delamination tip is dominated by shear stress component; applying loads such that two types of shear stress in the positive and negative directions are generated on the interface near the delamination tip; and obtaining apparent delamination propagating strengths in respective directions.

The second object can be attained by attaching the measured result of the adhesion strength obtained by the aforementioned means to the resin material.

The display method, the container and the carrying document for the resin material according to this invention feature to describe an adhesion strength based on shear stress of a resin against an adherend material together with the name of the adherend material, or to describe an adhesion strength of the resin against the adherend material by substantially excluding influences of residual stress.

In this case, the term "resin material" represents a resin material before being molded, and particularly in thermosetting resin it signifies a resin composition. Further, the term "resin" represents a cured product. The description is preferably made using a stress intensity factor or a strain energy release rate.

The stress intensity factor is typically represented in a unit of MPa $\sqrt{m}$ or kgf/mm$^{3/2}$, with dimensions of [(stress)× (length)$^{0.5}$], [(force)×(length)$^{-1.5}$], or [(mass)×(length)$^{-0.5}$× (time)$^{-2}$].

The strain energy release rate is typically represented by a unit of J/m$^2$ or kgf/mm, with dimensions of [(energy)× (length)$^{-2}$], [(force)×(length)$^{-1}$], or [(mass)×(time)$^{-2}$].

The method for measuring adhesion strength of resin material according to this invention features to comprise the steps of: forming a delamination portion between mutually adhered two materials; applying two types of loads respectively such that opposed shear stresses are generated to the adhering interface; obtaining a delamination propagating strength for each load, or adhering in layers two materials to be measured for adhesion strength; applying bending loads perpendicular to the adhering interface by inverting their directions such that opposed shear stresses are generated, or generating stresses in the same and opposed directions as and to that of the residual stress acting on the adhering interface to obtain the adhesion strength.

Thus, according to the present invention, since the adhesion strengths are obtained on the basis of the opposed shear stresses, the influences of the residual stress can be offset.

The method for manufacturing a composite body according to the present invention features to select a combination of a resin and a metal for forming the composite body on the basis of an adhesion strength of the resin obtained when the metal is used as an adherend material.

In this case, the resin is epoxy, and the metal is preferably selected from a group of copper, copper alloy, iron, aluminum or alloys thereof such as Fe-42 nickel etc. However, the resin is not limited to epoxy, but any thermoplastic resin or thermosetting resin can be used instead thereof. Further, it does not matter whether the resin material is liquid or powder and whether the curing is made by heat or any other factor. The adherend material is not limited to metal, but also may be ceramics or resin. Any form of cured product such as film, plate-type material or bulk may be used.

As the resin, thermosetting resins such as epoxy resin, silicone resin, and phenol resin, and thermoplastic resins such as polyethylene resin, polyamide resin are used. The resin may contain additives. Further, adhesives can be used as the resin e.g.: thermosetting resins such as epoxy resin basis; thermoplastic resins such as vinyl acetate-type resin basis; elastomers such as chloroprene basis; and mix-type resins such as phenol resin-epoxy resin and the like.

Furthermore, the strength display according to the present invention is advantageous particularly when applied to a composite body requiring to have a certain adhesiveness of resin to a metal, so as to be apt to electronic components such as resin encapsulated semiconductor devices, power equipments such as resin insulating transformer, and domestic electric appliances such as VTR chassis etc.

In this specification, the term "delamination propagating strength" stands for a strength against a propagation of a delamination from a previously delaminated portion as an onset point.

The display can be made together with other conditions.

By generating two types of i.e. forward and backward (positive and negative) shear stresses, it is possible to obtain two values of delamination propagating strength in two directions in that the residual stress increases and decreases the stress due to the load application. The apparent stress distribution near the delamination tip generated only by the load application can be accurately calculated from the dimensions, shapes and material properties of the specimen. Therefore, it is possible to obtain a universal true adhesion strength by arithmetically averaging these two values of apparent strength.

Namely, there is always any residual stress in an adhered product. Accordingly, in a measurement with a shear stress on the interface in the direction opposed to that of the residual stress, "true strength+residual stress" is measured. Meanwhile, in a measurement with a shear stress in the same direction as that of the residual stress, "true strength− residual stress" is measured. As a result, an average of these two resulting values, i.e. {(true strength+residual stress)+ (true strength−residual stress)}/2 would obviously represent the true strength. These principles are found by the present inventors.

Moreover, for resin materials, if such measured results of the adhesion strength are given, it would be possible to quantitatively predict and evaluate the adhesion reliability of molded products by analyzing stress occurring in molded state on the basis of conventionally used material property values such as Young's modulus and coefficient of linear expansion, and comparing thus obtained stress to the adhesion strength.

The above and other advantages, features and additional objects of this invention will be manifest to those versed in the art upon making reference to the following detailed description and the accompanying drawings in which a structural embodiment incorporating the principles of this invention is shown by way of illustrative example.

BRIEF DESCRIPTION OF THE DRAWINGS

FIG. 9 is a plan view showing a document carrying properties of a resin material containing a measured result of adhesion strength according to the present invention;

DETAILED DESCRIPTION OF THE PREFERRED EMBODIMENTS

Embodiments of the present invention will now be described with reference to the accompanying drawings.

Figure 1A:
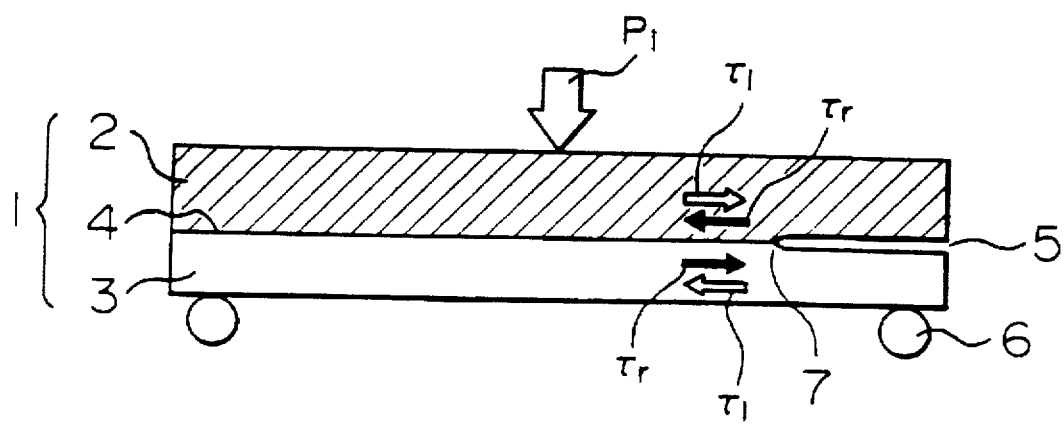
FIGS. 1A and 1B are front views showing a shape of a specimen and a load applying method in a method for measuring adhesion strength of resin materials according to an embodiment of the present invention.
Figure 1B:
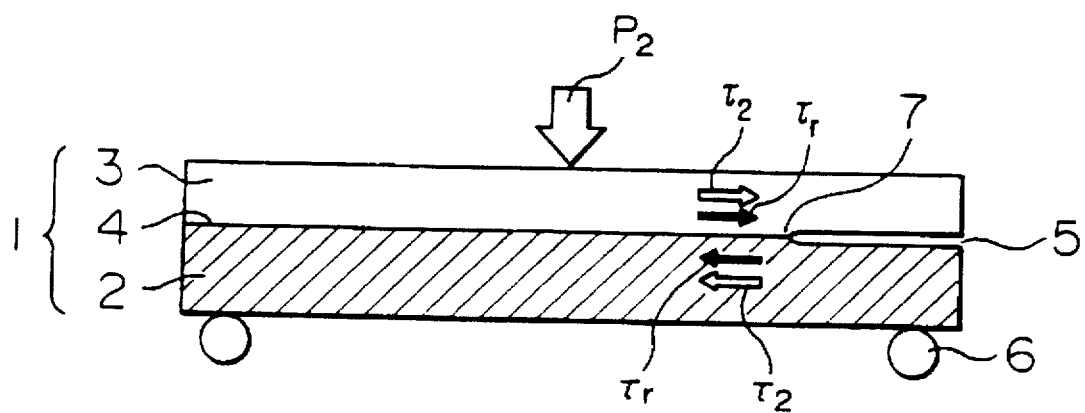

FIGS. 1A and 1B are front views showing a shape of a specimen and load applying methods in a method for measuring adhesion strength of resin materials according to an embodiment of the present invention.

A strip-type or square specimen 1 has a two-layer structure in which a resin 2 is adhered to an adherend 3. An end of the adhering interface 4 is previously provided with a delaminating portion 5. Such a type of specimen, which is subject to a bending load, is generally called ENF (End-Notched Flexure) specimen.

The resin material used in this embodiment is an epoxy resin composition that contains: cresol novolac epoxy resin as a main component; phenol novolac resin as a curing agent; fused silica as a filler; and a small amount of a plasticizer, a curing accelerator, a coupling agent, a mold release agent, a flame retarder, and a coloring agent.

For manufacturing the specimen 1, an adherend 3 is previously put in a mold die, and the resin 2 is molded at a high temperature and then cured and thereafter cooled to a room temperature, or heated or cooled to test temperatures.

Accordingly, residual stress $\tau_r$ is generated, mainly consisting of the shear stress component, due to cure shrinkage of the resin 2 and difference in coefficients of linear expansion between the resin 2 and the adherend 3. FIGS. 1A and 1B show acting directions of the residual stress $\tau_r$ near the delamination tip 7 in the case of the shrinkage or contraction of the resin 2 being larger than that of the adherend 3.

Adhesion strength tests were carried out by executing three-points bending tests for both cases of upwardly and downwardly inverting the specimen as shown in FIGS. 1A and 1B respectively, and measuring loads when the delamination propagation starts. Namely, in FIGS. 1A and 1B, the specimen 1 is supported by two supports 6 with the resin 2 side being set to the upper side, and a load $P_1$ is applied to the center of the span. In FIG. 1B, on the contrary, the adherend 3 side is set to the upper side, and in the same manner a load $P_2$ is applied.

As a result, near the delamination tip 7 of the adhering interface 4, shear stress $\tau_1$ generated by the load $P_1$ and shear stress $\tau_2$ generated by the load $P_2$ act in the directions as shown in FIGS. 1A and 1B respectively.

Figure 2A:
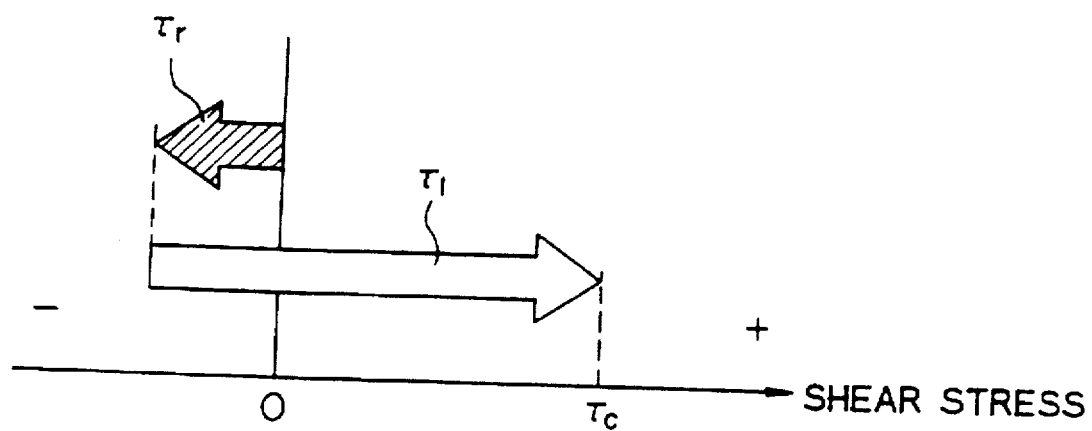
FIGS. 2A and 2B are schematic views showing relationships between stresses when delamination propagation starts.
Figure 2B:
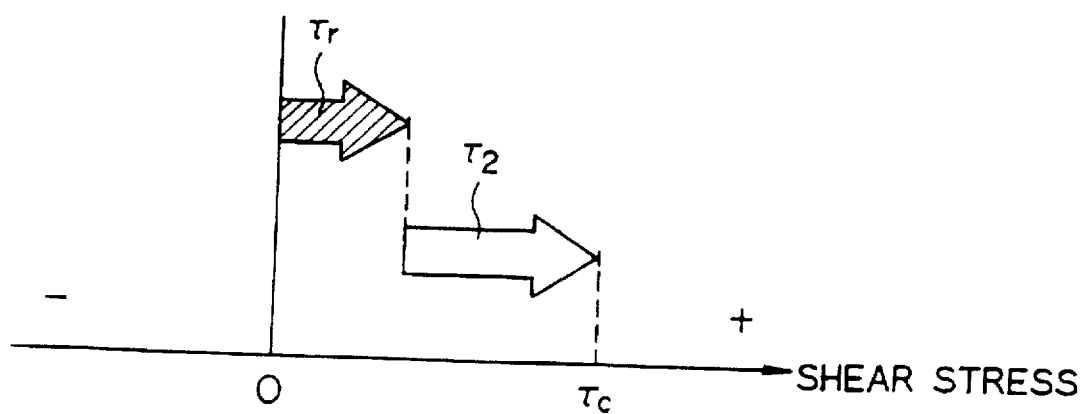

Schematic representation of the relationships between the stresses when the propagation of delamination starts in the case of FIGS. 1A and 1B are shown in FIGS. 2A and 2B.

In both cases of FIGS. 2A and 2B, the absolute value of the residual stress $\tau_r$ is identical, and the sign (positive or negative) is inverted only by an inversion of the coordinates. In FIG. 2A, when the load $P_1$ is applied, the shear stress $\tau_1$ generated by the load $P_1$ firstly reduces the residual stress $\tau_r$, and then inverts the sign, such that the propagation of the delamination starts upon the sum of both stresses $\tau_r$ and $\tau_1$ reaches a critical shear stress $\tau_c$ as a true adhesion strength.

On the other hand, in the case of FIG. 2B, the shear stress $\tau_2$ generated by the load $P_2$ acts to further increase the residual stress $\tau_r$, such that the summed stress reaches the critical stress $\tau_c$ with the load $P_2$ being smaller than the load $P_1$ in the case of FIG. 2A, and then the delamination starts.

In FIGS. 1A, 1B and 2A, 2B, the specimen 1 is upwardly and downwardly inverted with the identical applying direction of the loads $P_1$ and $P_2$. Meanwhile, if it is supposed that the load applying direction is inverted while coordinates are defined with the specimen 1 as a reference, the residual stress $\tau_r$ would be in the identical direction while the shear stresses $\tau_1$, $\tau_2$ generated by the loads are in the opposed directions for both FIGS. 1A, 2A and FIGS. 1B, 2B.

Figure 3:
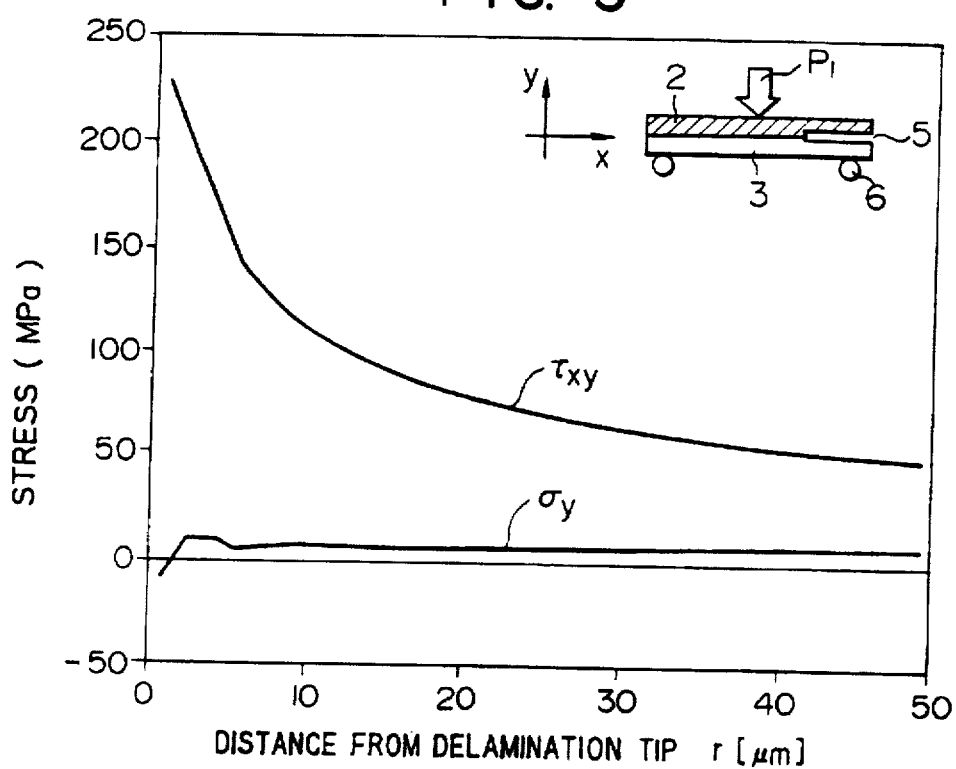
FIG. 3 is an explanatory view showing stress distributions near a delamination tip at a delamination propagating onset analyzed by finite element method in an adhering specimen of semiconductor encapsulating epoxy resin to a semiconductor lead frame Fe-42 Ni alloy plate.

FIG. 3 shows a result of stress distribution, analyzed by finite element method, near the delamination tip 7 along the adhering interface at an onset load of the delamination propagation which is measured when the load $P_1$ is applied from the resin 2 side as shown in FIG. 1A, for a specimen consisting of semiconductor encapsulating epoxy resin adhered to a semiconductor lead frame Fe-42 Ni alloy plate.

Fe-42 Ni alloy has a very small coefficient of linear expansion in comparison with a general resin material so as to have a large residual stress when used to make a specimen. Conventionally, it has been a particularly difficult material for the quantitative measurement of adhesion strength with resin material.

The dimensions of the specimen are: 55 mm of length; 6 mm of width; 1.5 mm of the resin thickness and 0.25 mm of the Fe-42 Ni alloy plate thickness; 45 mm of distance between the supports for 3-points bending test; and 10 mm of distance from a support at the delaminating portion side to the delamination tip. Such specimens having been molded at 175° C. and then cured are tested at room temperature.

The stress analysis was carried out taking account of both the thermal stress and the load application on the assumption that the residual stress is generated by cooling from the molding temperature to the room temperature.

FIG. 3 shows, with x-axis in the direction parallel to the interface 4 and y-axis in the direction perpendicular thereto as coordinates system for the specimen 1, distributions of normal stress $\sigma_y$ and shear stress $\tau_{xy}$ which are two stress components relating to the propagation of the delamination.

As shown in FIG. 3, near the delamination tip 7, the shear stress $\tau_{xy}$ is significantly larger than the normal stress $\sigma_y$, and it is understood that the propagation of the delamination largely depends on the shear stress component in the measuring method according to this embodiment.

Figure 4:
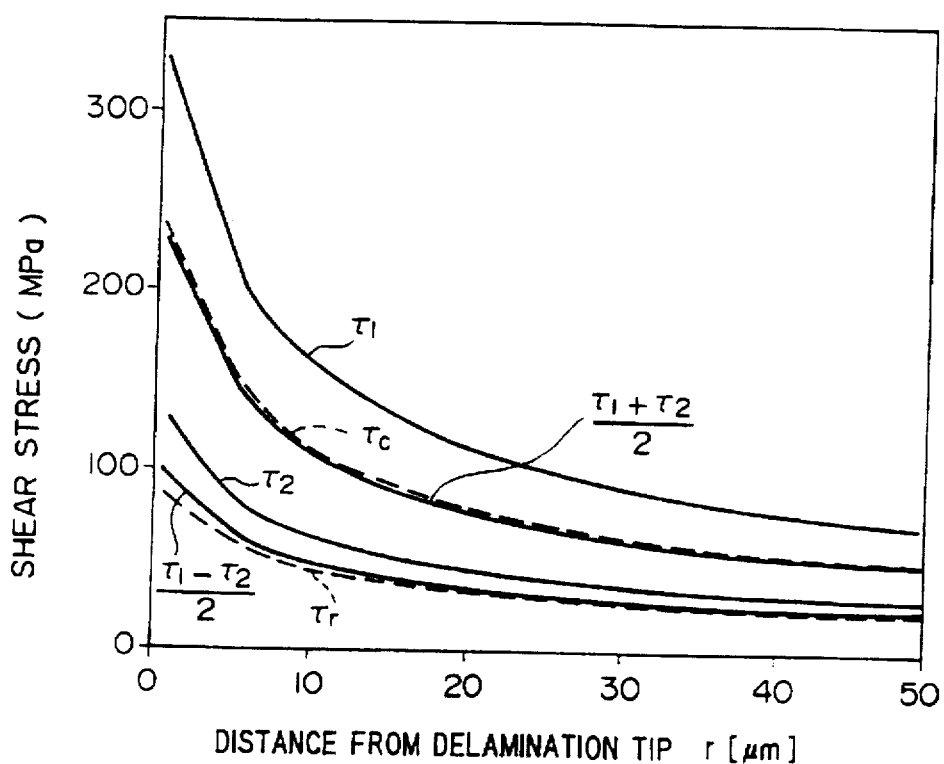
FIG. 4 is an explanatory view showing, in the same specimen as in FIG. 3, relationships between apparent stress distributions generated only by load application, thermal stress distribution, and a critical stress distribution as a true adhesion strength.

FIG. 4 shows an analyzed result of distribution of apparent shear stresses $\tau_1$, $\tau_2$ generated near the delamination tip by only the delamination propagation onset load measured with respect to two types of load applications shown in FIGS. 1A and 1B for the same specimen as in FIG. 3, and distribution of the shear stress $\tau_r$ generated by only the thermal stress, by use of finite element method.

Also, FIG. 4 shows a distribution of $(\tau_1+\tau_2)/2$ and $(\tau_1-\tau_2)/2$, and distribution of the critical stress $\tau_c$ at the onset of delamination propagation equivalent to $\tau_{xy}$ in FIG. 3. As can be seen from FIG. 4, the arithmetic average $(\tau_1+\tau_2)/2$ of the apparent shear stresses $\tau_1$ and $\tau_2$ generated by only the load application agrees well with the critical stress $\tau_c$ at the onset of delamination propagation, while $(\tau_1-\tau_2)/2$ agrees with the shear stress $\tau_r$ generated only by the thermal stress.

Accordingly, it is possible to separate the critical shear stress $\tau_c$ as the true adhesion strength from the residual stress $\tau_r$ by calculating the apparent shear stresses $\tau_1$ and $\tau_2$ for both cases of inverting upwardly and downwardly the specimen 1 as shown in FIGS. 1A and 1B.

The distribution of the critical shear stress $\tau_c$ obtained as aforementioned is not a single value so as to be improper to be directly used as the true adhesion strength. Therefore, as a parameter representing the stress distribution at the delamination tip as shown in FIG. 3, fracture mechanics parameters such as stress intensity factor and Strain energy release rate are used.

The stress distribution on the interface near the delamination tip can be expressed by use of the stress intensity factors $K_I$ and $K_{II}$ for opening-type (mode I) land in-plane shear-type (mode II) deformation, as follows:

$$\sigma_y + i\tau_{xy} = (K_I + iK_{II})(2\pi r)^{-1/2}(r/d)^{i\alpha} \quad (1)$$

$$\alpha = \frac{1}{2\pi} \log_e \left\{ \left(\frac{K_p}{\mu_p} + \frac{1}{\mu_a}\right) / \left(\frac{K_p}{\mu_p} + \frac{1}{\mu_a}\right) \right\} \quad (2)$$

$$K_j = \begin{cases} 3 - 4v_j & : \text{plane strain} \\ (3 - v_j)/(1 + v_j) & : \text{plane stress} \end{cases} \quad (3)$$
$$(j = p, a)$$

where
$\sigma_y$: normal stress
$\tau_{xy}$: shear stress
r: distance from delamination tip $\pi$: number $\pi$
i: imaginary unit
d: representative length The characters $\mu$ and $\upsilon$ represent the shear modulus and Poisson's ratio respectively. The resin and the adherend are mutually distinguished by subscripts p and a respectively.

As shown in the equation (1), the critical stress distribution equivalent to the true adhesion strength can be expressed by combining two parameters $K_I$ and $K_{II}$.

In the case of interface formed of different kinds of materials, unlike in the case of the cracks in homogeneous materials, $K_I$ and $K_{II}$ do not correspond to $\sigma_y$ and $\tau_{xy}$ respectively, as represented by the equation (1). Therefore, both of these values cannot be separately considered.

So even when the shear stress component is dominant as in this embodiment, the stress distribution cannot be represented only by $K_{II}$, such that a combination of $K_I$ and $K_{II}$ should be used.

As a method for representing the stress distribution near the delamination tip by a single parameter, it has been known a method using a stress intensity factor $K_i$ expressed by an equation noted below for a case of the residual stress being absent. This is disclosed in a thesis in the Proceedings of the 67th Spring Annual Meeting of the Japan Society of Mechanical Engineers previously noted.

$$K_i = \sqrt{K_I^2 + K_{II}^2} = \lim_{r \to 0} \sqrt{2\pi r} \sqrt{\sigma_y^2 + \tau_{xy}^2} \quad (4)$$

This parameter can be also applied to the separation of the true adhesion strength from the residual stress previously mentioned, and is capable of being easily calculated and evaluated in comparison with the case using the combination of $K_I$ and $K_{II}$.

Namely, since there is a relationship of $\tau_{xy} > \sigma_y$ as shown in FIG. 3, $K_i$ can be represented as the following equation (5) so as to correspond to the distribution of the shear stress $\tau_{xy}$ one to one.

$$K_i = \lim_{r \to 0} \sqrt{2\pi r} \sqrt{\sigma_y^2 + \tau_{xy}^2} \approx \lim_{r \to 0} \sqrt{2\pi r} \, \tau_{xy} \quad (5)$$

When the specimen is vertically inverted as shown in FIGS. 1A and 1B to render the apparent $K_i$ only by the applied loads $P_1$ and $P_2$ (hereinafter referred to as $K_{i1}$ and $K_{i2}$), it is possible to calculate $K_i$ corresponding to the true adhesion strength (hereinafter represented by $K_{ic}$) from their arithmetic average $(K_{i1}+K_{i2})/2$, and $K_i$ corresponding to the residual stress (hereinafter represented by $K_{ir}$) from $(K_{i1}-K_{i2})/2$, such that the adhesion strength can be evaluated from a single value.

$K_i$ value for a desired load condition may be calculated on the basis of the stress distribution on the interface or the displacement distribution on the delamination surface near the delamination tip analyzed by numerical analysis such as finite element method or boundary element method. The calculating method is disclosed in the Transactions of the Japan Society of Mechanical Engineers, Ser. A, Vol. 55, No. 510 (1989) pp. 340–347.

$K_i$ value for the load application in the embodiment shown in FIGS. 1A and 1B may also be readily calculated using beam theory, without executing the numerical analysis, in the same manner as in the case of the strain energy release rate mentioned later.

Figure 5:
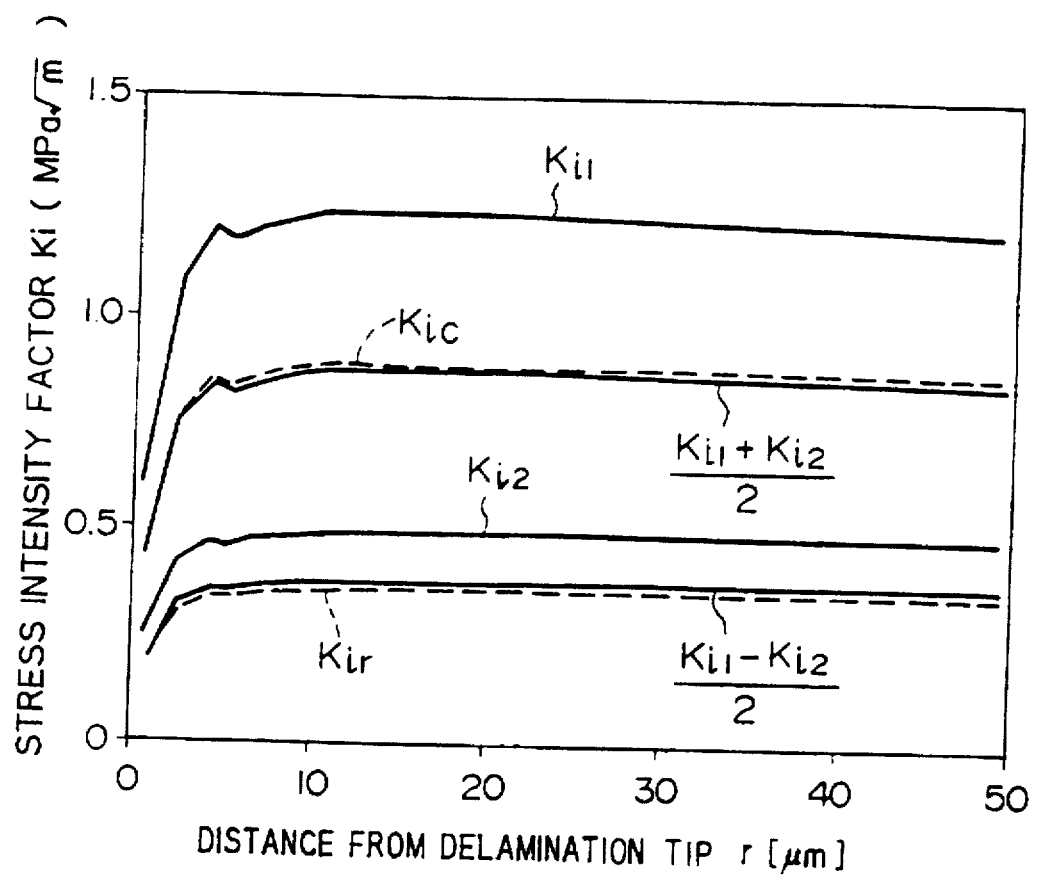
FIG. 5 is an explanatory view showing, in the same specimen as in FIG. 3, relationships between apparent stress intensity factors generated only by load application, a stress intensity factor only by a thermal stress, and a critical stress intensity factor as a true adhesion strength.

FIG. 5 shows calculated results of: apparent stress intensity factors $K_{i1}$, $K_{i2}$ only by the load application; stress intensity factor $K_{ir}$ only by the thermal stress; and stress intensity factor $K_{ic}$ corresponding to the critical stress when the propagation of the delamination starts, taking account of both the load and the thermal stress.

Although there are somewhat large numerical analysis errors just near the delamination tip in other regions all the stress intensity factors are substantially constant.

As shown in FIG. 5, it is understood that the values $(K_{i1}+K_{i2})/2$ and $(K_{i1}-K_{i2})/2$ agree well with the stress intensity factors $K_{ic}$ and $K_{ir}$ corresponding to the true adhesion strength and the residual stress, respectively.

In this embodiment, the residual stress and the true adhesion strength are obtained by thermal stress analysis. For certain types of resin materials, however, it is sometimes necessary to measure, in advance of the analysis, detailed temperature-dependent data of properties such as coefficient of thermal expansion or Young's modulus corresponding to a thermal history from the specimen molding to the adhesion strength test, due to the conspicuous temperature dependency of the material properties. In another case, further, significant viscoelastic behavior of the material at high temperatures would sometimes make the analysis very complicated or make accurate residual stress analysis difficult.

According to this embodiment where the residual stress is separated and eliminated only by using the apparent $K_i$'s with respect to the load application, the true adhesion strength can be readily and accurately obtained without analyzing the residual stress.

Further, since the stress intensity factor $K_i$ can uniquely represent the intensity of the stress near the delamination tip, a universal adhesion strength independent of the dimensions and shapes of the specimen can be obtained.

The $K_i$ value for the load application in the embodiment shown in FIGS. 1A and 1B can be derived using beam theory in the following manner. Namely, the deflection at the loading point when a load P is applied to the center between the supports 6 can be represented as the following equation (6), wherein: b, width of the specimen 1; $t_p$, thickness of the resin 2; $t_a$, thickness of the adherend 3; 2L, distance between the supports in three-point bending; a, distance from the support 6 at the side of the delaminating portion 5 to the delamination tip 7; $E_p$, Young's modulus of the resin 2; $E_a$, Young's modulus of the adherend 3.

$$\delta = \frac{P}{b} \left\{ \frac{a^3}{t_p{}^3 E_P + t_a{}^3 E_a} + \frac{(t_P E_P + t_a E_a)(2L^3 - a^3)}{4 t_P t_a E_P E_a (t_P + t_a)^2 + (t_P{}^2 E_P - t_a{}^2 E_a)^2} \right\} \quad (6)$$

Since the compliance C for the load P is expressed as $\delta/P$, the strain energy release rate G can be obtained as follows:

$$G = \frac{P^2}{2b} \frac{dc}{da}$$
$$= \frac{3P^2 a^2}{2b^2} \left\{ \frac{1}{t_P{}^3 E_P + t_a{}^3 E_a} - \frac{t_P E_P + t_a E_a}{4 t_P (t_a E_P E_a (t_P + t_a)^2 + (t_P{}^2 E_P - t_a{}^2 E_a)^2)} \right\} \quad (7)$$

There is a following relationship between the stress intensity factor $K_i$ and the strain energy release rate G:

$$K_i = 4\cosh(\alpha \pi) \sqrt{\frac{G}{(K_P + 1)/\mu_P + (K_a + 1)/\mu_a}} \quad (8)$$

Accordingly, the stress intensity factor $K_i$ can be easily arithmetically calculated from the equations (7) and (8).

There is a following relationship between the Young's modulus E, the shear modulus $\mu$, and the Poisson's ratio $\nu$. For the calculation, two of these three should be previously calculated.

$$\mu = \frac{E}{2(1+\nu)} \quad (9)$$

The material property values necessary for the analysis of the apparent stress or the stress intensity factor generated only by the load are only these values of material properties at the test temperature regardless of the thermal history from the molding temperature etc.

The aforementioned strain energy release rate G can also be used as a parameter representing the true adhesion strength instead of the stress intensity factor $K_i$.

In this case, the strain energy release rate G is proportional to a square of the stress intensity factor $K_i$ and that of the stress. For calculating the strain energy release rate $G_c$, $G_r$ corresponding to the true adhesion strength and the residual stress from the apparent strain energy release rate $G_1$, $G_2$ for the loads $P_1$ and $P_2$, it is necessary to execute the following additional and subtractive calculations for the square roots:

$$G_c = \left( \frac{\sqrt{G_1} - \sqrt{G_2}}{2} \right)^2 \quad (10)$$

$$G_r = \left( \frac{\sqrt{G_1} - \sqrt{G_2}}{2} \right)^2 \quad (11)$$

For representing the true adhesion strength, in addition to the aforementioned stress intensity factor $K_I$, $K_{II}$, the stress intensity factor $K_i$, and the strain energy release rate G, any other parameters capable of uniquely representing the intensity of the stress near the delamination tip regardless of the dimensions and shapes of the specimen, such as path-independent integral J used in fracture mechanics can be used.

In practice, it is also possible to use values of the delamination propagation onset loads from opposed directions, or a value of the averaged delamination propagation onset load of the opposed loads with the same delamination distance in a condition of a predetermined dimension and shape of the specimen.

These load values can also be converted into desired universal parameters, if necessary.

Any of the thermosetting and thermoplastic resin materials can be used for the adhesion strength measurement. Further, it is possible to use as the adherend material apart from the metal, inorganic materials such as ceramics, silicon and glass etc., other resin materials, and the same but separately formed resin material. Residual stresses other than thermal stress caused by any reason such as shrinkage at the curing reaction, swelling due to permeation of water or chemical liquid etc., and material alteration due to physical or chemical environmental factors and the like can also be separated.

On determination of the dimensions of the specimen 1, the following conditions should be satisfied:

(1) The interface 4 is not delaminated by the residual stress at the stage of making the specimen 1;

(2) The resin 2 and the adherend 3 are not fractured or plastically deformed in advance of the delamination of the interface;

(3) Any large deformation, which would be out of the application of beam theory or linear numerical analysis does not take place at the bending test; and (4) The influence of the shear stress acting in the width direction of the specimen 1 i.e. in the direction perpendicular to the page plane of FIGS. 1A and 1B can be ignored.

For the condition (1) the resin 2 is preferably thinner as far as possible than the length or the width of the specimen. Meanwhile, on the contrary, for the conditions (2) and (3) the resin 2 should not be preferably too thin compared to the distance between the supports in three-points bending. For the condition (4), it is preferable to set the width of the specimen 1 to a sufficiently small value in comparison with the distance between the supports.

The critical values of the dimensions satisfying the above conditions depend on the combination of the kinds of the resin 2 and the adherend 3, but it could be present the general measures as follows:

The thickness of the specimen is preferably in a range of 1/5–1/40 of the distance between the supports, and the width of the specimen is preferably not exceeding 1/5 of the distance between the supports; and The delamination tip 7 is preferably separated from both the support 6 and the loading point by a distance equal to or more than the thickness of the specimen.

To form the delaminating portion 5 at one end of the specimen 1 in advance of the adhesion strength test in FIGS. 1A and 1B, a mold release agent is coated on one end of the adherend 3 before molding the specimen 1, or a tape made of less adhesiveness material such as fluororesin is applied thereon.

Without using such delaminating means before molding, also, it is possible to form the delaminating portion by previously reducing the distance between the supports 6 before the adhesion strength test and applying a local bending load to near the end portion of the specimen 1, or pressing a razor blade to the end portion of the specimen 1.

Even in the case of using the delaminating means before molding, it is preferable to further propagate a natural delamination from the tip of the resulting delaminated portion by applying a bending load etc. in order to enable more accurate measurement of the adhesion strength without being disturbed by the applied tape etc.

The length of the delaminating portion 5 which is necessary to calculate the stress intensity factor $K_i$ and the like may be measured through a microscope observation of the side surface of the specimen, or an ultrasonic inspection from the upper or the lower surfaces. When the delaminating means is used before molding the specimen, it is also possible to measure the coated length of the mold release agent or the applied length of the tape. But the latter case is premised on that the delamination is not propagated after the molding.

The onset of the propagation of the delamination in the three-points bending test can be detected by a change in the compliance C due to the change in the delamination length, i.e. a folding of a curve representing the relationship between the load P and the deflection δ. Alternatively, it is also possible to detect acoustic signals generating upon the onset of delamination propagation through an acoustic emission detector or a microphone etc.

In the aforementioned example, the adhesion strength has been obtained based on the propagation onset of the delamination. However, in certain materials, the stress intensity factor $K_i$ and the like sometimes vary depending on the states of the propagation such as propagation onset time, during the propagation, propagation stopping time. In such a case, the stress intensity factor value at a proper time point may be used in accordance with the use of the required adhesion strength.

Figure 6:
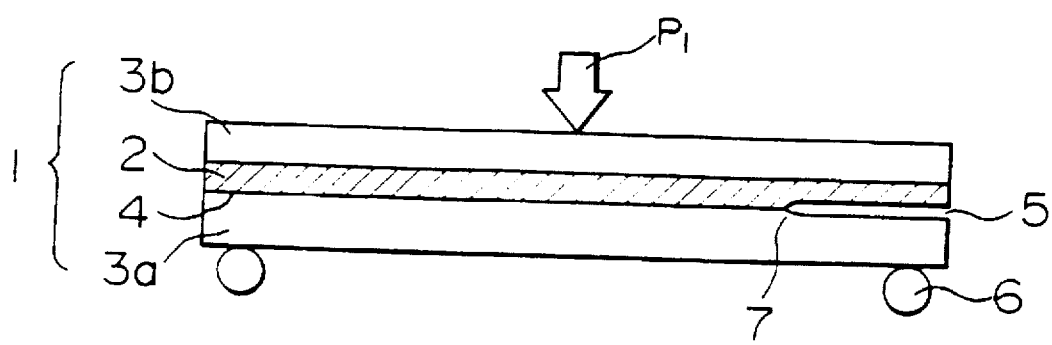
FIG. 6 is a front view showing a configuration of a specimen and a load applying manner in a method for measuring adhesion strength of resin material according to a second embodiment of the present invention.
Figure 7:
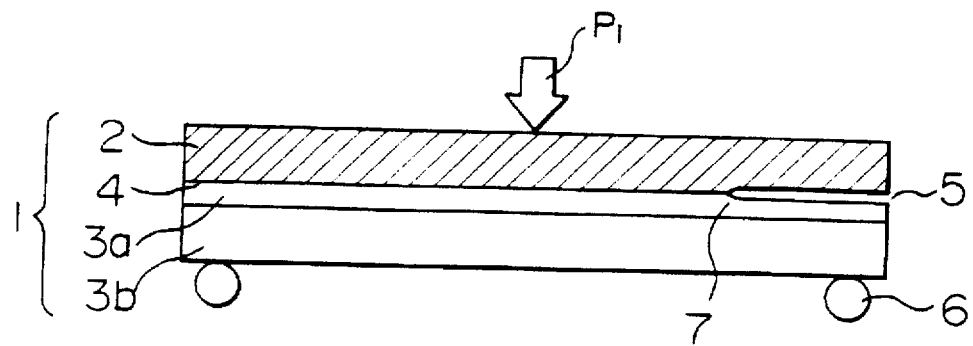
FIG. 7 is a front view showing a configuration of a specimen and a load applying manner in a method for measuring adhesion strength of resin material according to a third embodiment of the present invention.

FIGS. 6 and 7 are front views showing a configuration of the specimen and a load applying manner respectively, in a method for measuring adhesion strength of resin material according to further embodiment of the present invention.

The specimen used in the present method need not be composed of only two materials, the resin 2 and the adherend 3 being the medium for the mutual adhesion strength test. For example, as shown in FIG. 6, it is also possible to measure an adhesion strength of the resin 2 held between the same or different two adherend 3a and 3b at the interface 4 of the material 3a side, or to measure an adhesion strength of the resin 2 to the second adherend 3a formed on the surface of the first adherend 3b by plating, adhesion or deposition or the like as shown in FIG. 7.

Moreover, not limited to such two-layer and three-layer structures as shown in FIGS. 1A and 1B, 6 and 7, it is also possible to use a multilayered structure with equal to or more than four layers, or a structure that a particular material is present only in a part of the entire length of the specimen. In these cases, the delaminating portion 5 should be formed at the interface 4 between the materials to be served for the adhesion strength measurement.

In FIGS. 6 and 7, the load applying manner for applying the load $P_1$ only from one direction respectively is shown. However, in the same manner as in the case of the embodiment shown in FIGS. 1A and 1B, the three-points bending test is carried out for both cases of inverting the specimen upwardly and downwardly and the true adhesion strength is separated from the residual stress.

Figure 8A:
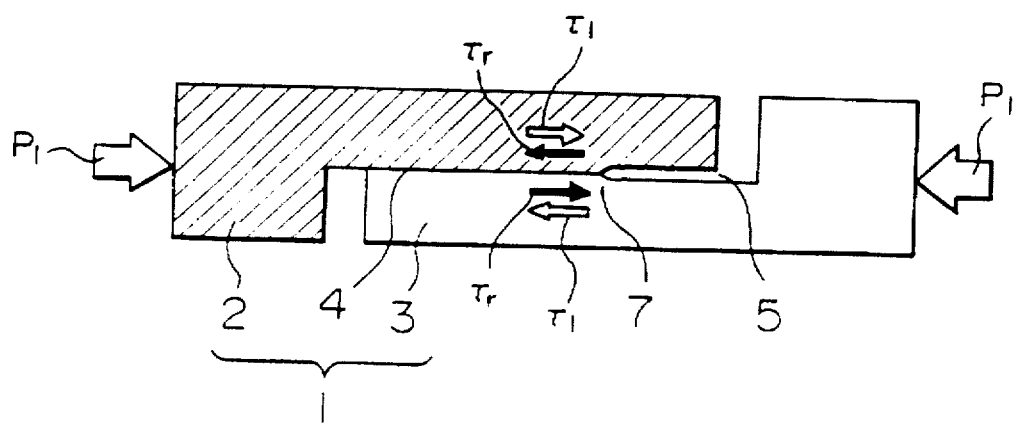
FIGS. 8A and 8B are front views showing a configuration of a specimen and load applying manners in a method for measuring adhesion strength of resin material according to a fourth embodiment of the present invention.
Figure 8B:
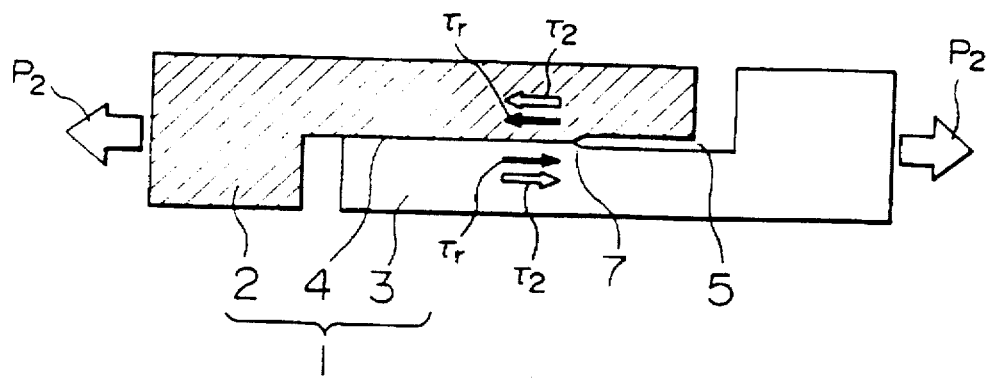

FIGS. 8A and 8B are front views showing a configuration of the specimen and load applying manners in a further different embodiment of this invention.

In this embodiment, a compressive load $P_1$ as shown in FIG. 8A and a tensile load $P_2$ as shown in FIG. 8B are applied in the direction parallel to the interface 4 of the specimen composed of mutually adhered resin 2 and the adherend 3 to generate mutually inverted shear stresses $\tau_1$ and $\tau_2$.

Thus, according to this embodiment, specimens of any configuration and any load applying manner may be used so long as the shear stresses near the delamination tip 7 can be mutually inverted and the shear stresses can be set to a value sufficiently larger than that of the normal stress generating perpendicularly to the interface 4.

When the compressive and tensile loads are applied as shown in FIGS. 8A and 8B, for reducing the normal stress component, the loads to be applied at both ends of the specimen 1 in the opposed directions should be on a single axial line and the specimen 1 should not be subject to the bending moment.

When the adhesion strength test is executed by bending load, apart from the three-points bending load method shown in FIGS. 1A and 1B etc., a variety of load applying manners such as four-points bending load method, or a method of applying a bending load to a cantilever-supported specimen and the like. In these cases, the stress intensity factor $K_i$ and the strain energy release rate G are calculated through beam theory.

FIG. 9 is an example of a document carrying properties of the resin material as a result of the adhesion strength measurement according to the present invention.

If material property values such as conventionally used Young's modulus or bending elastic modulus instead thereof, Poisson's ratio and coefficient of linear expansion etc. for both the resin material and the adherend material are measured or given, the stress generating on the adhering interface inside a completed resin molded product etc. can be predicted by analysis.

Accordingly, if the true adhesion strength represented by parameters such as $K_i$ obtained through the present method is given in the form of the document shown in FIG. 9, it is possible to quantitatively predict and evaluate the presence/ absence of the delamination at the interface and the degree of the delamination by comparing the adhesion strength and the predicted result of the stress, without need of actually making a completed product of the resin material.

In the present invention, the adhesion strength against the delamination propagation in case of already existing the delaminating portion is obtained. Therefore, for predicting the presence/absence of the delamination within a product on the basis of the above adhesion strength, presence of a small delaminating portion is supposed, and presence/ absence of the propagation of the delamination therefrom is evaluated.

While the conventional adhesion strength could be used only for relative comparison between materials because of its dependency on the dimensions and configuration of the specimen, the adhesion strength measured by the present method can be applied to the quantitative evaluation of the adhesion reliability of molded product. Therefore, for describing the measured result, the measuring method such as a method using three-points bending test by upward and downward inversion or a method using inversion of shear stress may be preferably noted.

The measured result of the adhesion strength may be also described, in addition to the test records as shown in FIG. 9, on a variety of specifications of the resin material and on the container, so as to enable the prediction and the evaluation of the adhesion reliability of the resin material.

As aforementioned, Poisson's ratio of the resin is necessary for the analysis of the generating stress. But since it is more complicated to measure the Poisson's ratio compared to the bending elastic modulus or the like and this ratio has an insignificant influence on the stress analysis result, the description of Poisson's ratio may be omitted from description as in the example shown in FIG. 9.

The adhesion strength of the resin varies depending on the kind or the surface state of the adherend, environmental conditions such as temperature and humidity, and molding conditions. Therefore, the measured results of the adhesion strength may preferably be noted in numerical values together with the such conditions, or represented in the form of graphs with respect to such conditions as temperatures etc.

Figure 10:
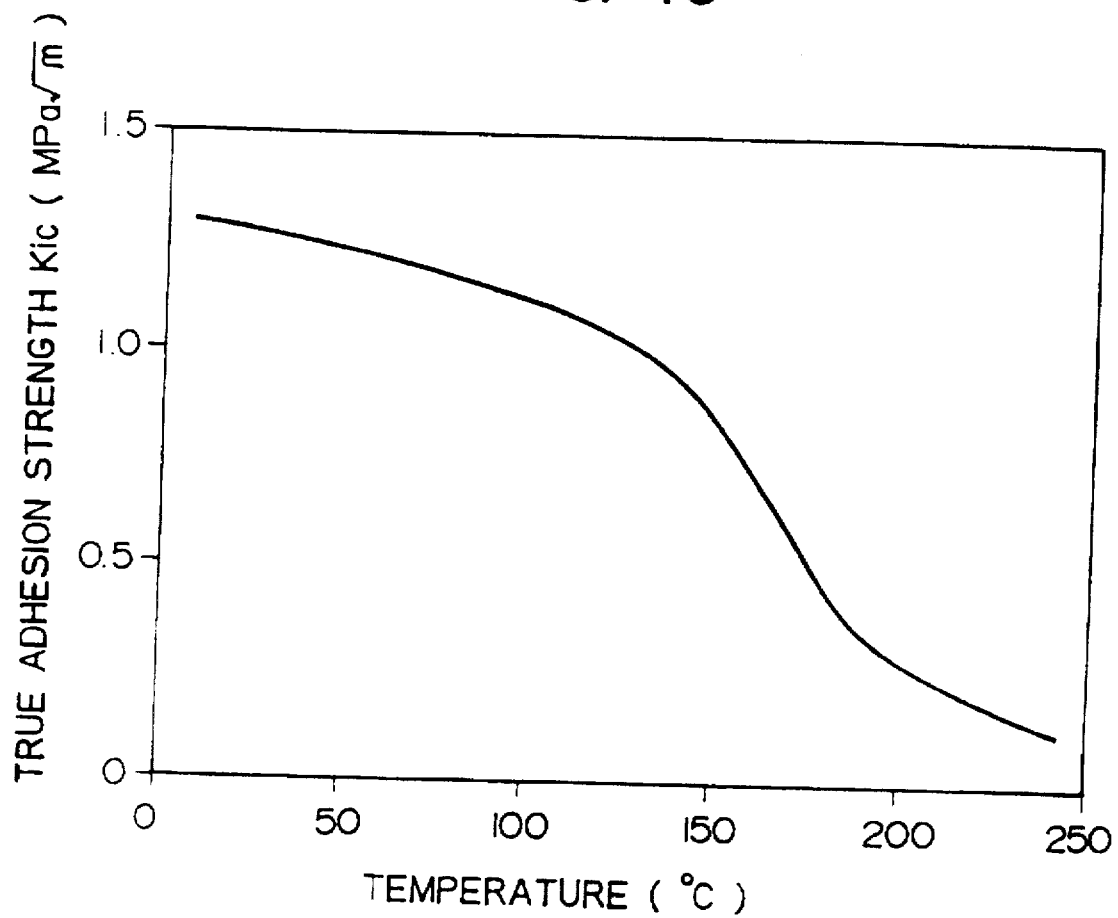
FIG. 10 is graphic view showing temperature dependence of true adhesion strength of a semiconductor encapsulating epoxy resin to a semiconductor lead frame Fe-42 Ni alloy plate.

FIG. 10 is a graphic diagram showing temperature dependence of true adhesion strength $K_i$ of semiconductor encapsulating epoxy resin to a semiconductor lead frame Fe-42 Ni alloy plate obtained according to the present invention.

In the conventional method for measuring adhesion strength, the temperature dependency of the adhesion strength could not be quantitatively calculated since not only the true adhesion strength but also the residual stress changed in accordance with the temperature. According to the present invention, meanwhile, if the true adhesion strength is given in the form of a function of temperature, the critical temperature of the delamination generation can be predicted by being compared to the generating stress of the molded product calculated by the analysis as the function of temperature.

According to the present invention, two kinds of adhesion strength, i.e. when the residual stress is added to and subtracted from the stress caused by the load application can be provided and the stress distribution at the interface can be taken account. In consequence, the true adhesion strength can be separated from the residual stress without executing any analysis of the residual stress, and universal adhesion strength can be accurately and readily measured independently from the dimensions and configuration of the specimen.

Furthermore, in this invention, since the stress of the product obtained through analysis and the true adhesion strength can be compared, the reliability of the interface inside the molded product can be predicted and evaluated without actually making the molding product.

Next, there will now be shown an example where a delamination generating temperature, at an adhering interface between a lead frame and a sealing resin when a resin-sealed type semiconductor device is heated, is predicted from an adhesion strength, according to this invention.

Figure 11:
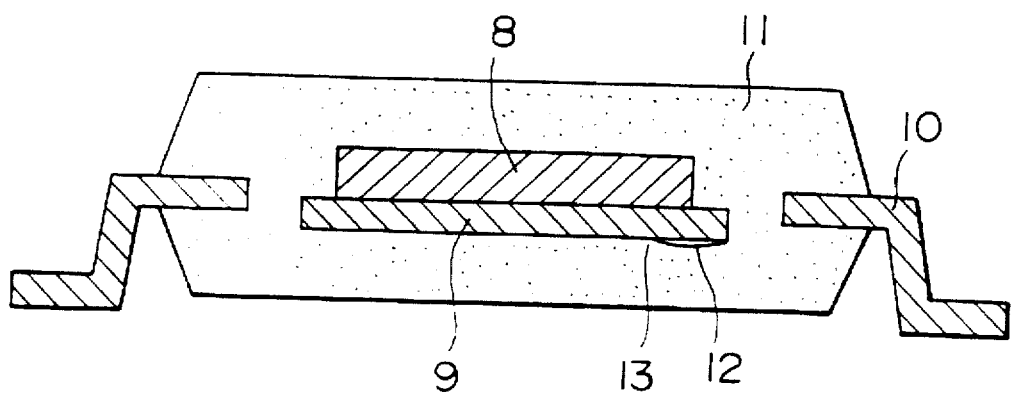
FIG. 11 is a cross-sectional view showing a resin-sealed type semiconductor device in which a delamination generating temperature at the interface is predicted from the adhesion strength, according to the present invention.

In FIG. 11, a semiconductor element 8 is fixed to a tab 9 portion of a Fe-42 Ni alloy lead frame by adhesive agent or the like. A plurality of leads 10, made of the same material, are formed around the tab 9. The electrode and the leads 10 are mutually in electrical connection through fine metal lines not shown. These components are molded by epoxy sealing resin 11, except external coupling portions of the leads 10.

Such a resin-sealed type semiconductor device as shown in FIG. 11 is exposed to a high temperature of equal to or more than 200° C. when mounted on a wiring substrate by soldering. Thermal stress generating at this time would cause delamination at interfaces in the semiconductor device. In order to evaluate the delimination criteria, it is useful to apply the stress intensity factor $K_i$ at the delamination tip. Therefore, a small delaminating portion 12 is assumed at an end portion of an adhering interface between the sealing resin 11 and the lower surface of the tab 9. Values of the stress intensity factor $K_i$ generating at the delamination tip 13 when the resin-sealed type semiconductor is heated at a variety of temperature are analyzed using finite element method. Further, true adhesion strength value $K_{ic}$ at various temperatures between the sealing resin 11 and the lead frame material are measured so as to be compared to the aforementioned analyzed value.

Figure 12:
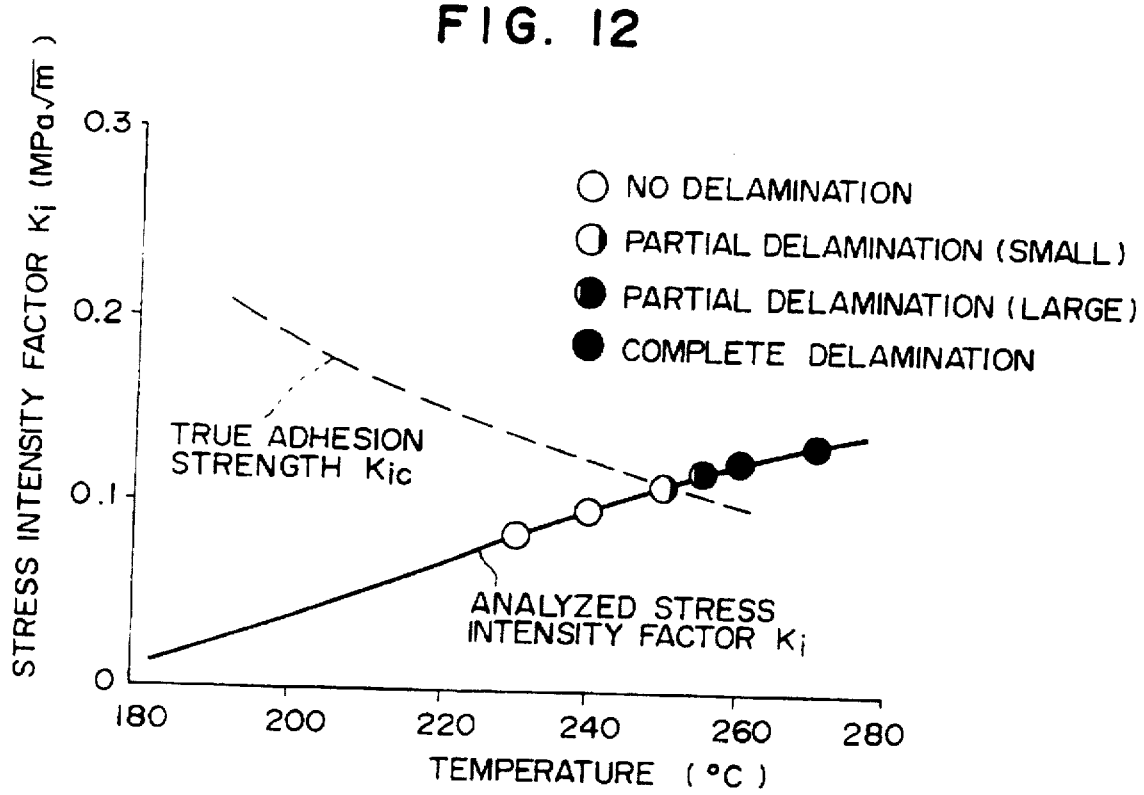
FIG. 12 is an explanatory graphic diagram showing predicted delamination generating temperatures in the resin-sealed type semiconductor device shown in FIG. 11.

FIG. 12 shows the compared result. In FIG. 12, the increasing curve (left down-right up) represents an analyzed relationship between the generated stress intensity factor $K_1$ and the heating temperature, while the decreasing curve (left up-right down) represents an experimentally obtained relationship between the true adhesion strength $K_{ic}$ and the measuring temperature. The intersecting point of both curves represents a generating temperature of the delaminating propagation. A variety of marks on the curve representing the analyzed stress intensity factor $K_i$ in FIG. 12 show states of delaminating generation at the lower surface of the tab 9 observed, through an ultrasonic inspecting apparatus after an actual resin-sealed type semiconductor device is put in an isothermal vessel for ten minutes. The white circle indicates a sample without showing any delamination at the lower surface of the tab 9 at that temperature, the black circle indicates a sample with a total delamination of the lower surface of the tab 9 at that temperature. And, the white-black mixed circles indicate partial delamination of the portions near the end of the lower surface of the tab 9, in which the size of the delamination is represented by way of the ratio of the black region to the white region in the circle.

As can be seen from FIG. 12, no delamination is observed at temperature regions where the generated stress intensity factor $K_i$ is less than the true adhesion strength $K_{ic}$, a total delamination is observed at temperature regions where $K_i$ is higher than the true adhesion strength $K_{ic}$, and partial delamination is observed at temperature regions near the intersecting point of both curves. These results indicate that the generation of the delamination inside the resin-sealed semiconductor device can be predicted by comparison of the adhesion strength obtained according to this invention with the analyzed stress intensity factor of the resin-sealed type semiconductor device.

If the generation of the delamination can be quantitatively predicted as mentioned above, it is possible to select optimum resin material, lead frame material, surface treating conditions e.g. plating for the lead frame, resin molding conditions and conditions for combining thereof, without actually making molded products of the resin material.

What is claimed is:

1. A method for displaying a value of a strength of a resin material, comprising displaying a value of an adhesion strength based on shear stress of a resin against an adherend material, said adhesion strength being displayed together with a name of the adherend material, wherein said adhesion strength is measured by a measuring method comprising steps of:

forming a delamination portion at an adhering interface between said resin and an adherend;

applying two types of loads respectively such that opposed shear stresses are generated to the adhering interface; and obtaining a delamination propagating strength for each of the loads.

2. A method according to claim 1, wherein said resin is a cured product, and said resin material is a resin composition.

3. A method according to claim 1, wherein said display is made by use of a stress intensity factor.

4. A method according to claim 1, wherein said display is made by use of a strain energy release rate.

5. A method for displaying a value of a strength of a resin material, comprising displaying a value of an adhesion strength of a resin against an adherend material obtained by substantially excluding influences of residual stress, wherein said adhesion strength is measured by a measuring method comprising steps of:

forming a delamination portion at an adhering interface between said resin and an adherend;

applying two types of loads respectively such that opposed shear stresses are generated to the adhering interface; and obtaining a delamination propagating strength for each of the loads.

6. A method according to claim 5, wherein said resin is a cured product, and said resin material is a resin composition.

7. A method according to claim 5, wherein said display is made by use of a stress intensity factor.

8. A method according to claim 5, wherein said display is made by use of a strain energy release rate.

* * * * *